US012647679B2

(12) United States Patent
Filiciotto et al.

(10) Patent No.:   US 12,647,679 B2
(45) Date of Patent:       Jun. 2, 2026

(54) TECHNIQUES FOR SIMULTANEOUSLY RUNNING DISCRETE IMAGING MODALITIES

(71) Applicant: GYRUS ACMI, INC, Westborough, MA (US)

(72) Inventors: Frank Filiciotto, Bethlehem, PA (US); Dawei Liu, Sharon, MA (US); Thorsten Juergens, Hamburg (DE)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 18/295,961

(22) Filed: Apr. 5, 2023

(65) Prior Publication Data

US 2023/0379578 A1     Nov. 23, 2023

Related U.S. Application Data

(60) Provisional application No. 63/364,814, filed on May 17, 2022.

(51) Int. Cl.
H04N 23/667       (2023.01)
A61B 1/00         (2006.01)
(Continued)

(52) U.S. Cl.
CPC ....... H04N 23/667 (2023.01); A61B 1/00009 (2013.01); A61B 1/0005 (2013.01);
(Continued)

(58) Field of Classification Search
None
See application file for complete search history.

(56) References Cited

U.S. PATENT DOCUMENTS

2007/0036402 A1* 2/2007 Cahill .................. G06T 7/0012
                                                      382/128
2013/0012794 A1* 1/2013 Zeng .................... A61B 1/0684
                                                      600/179
(Continued)

FOREIGN PATENT DOCUMENTS

CN        209172253       7/2019
CN        119234248 A     1/2025
(Continued)

OTHER PUBLICATIONS

"International Application Serial No. PCT US2023 017526, International Search Report mailed Jul. 17, 2023", 5 pgs.
(Continued)

*Primary Examiner* — Heather R Jones
(74) *Attorney, Agent, or Firm* — Schwegman Lundberg & Woessner, P.A.

(57)             ABSTRACT

A system and processing techniques for simultaneously analyzing multiple imaging modalities. The discussed technique can include capturing a combined image stream including a first modality stream and at least a second modality stream. The technique continues by analyzing the first modality stream with a first analysis module and, concurrently, analyzing a second modality stream with a second analysis module. The combined image stream can be generated using timed lighting modalities to generate interleaved image streams or by extracting narrow color bands from a primary color sensor.

21 Claims, 9 Drawing Sheets

(51) Int. Cl.

| | | |
|---|---|---|
| *A61B 1/06* | (2006.01) | |
| *G06T 7/00* | (2017.01) | |
| *G06T 7/73* | (2017.01) | |
| *H04N 23/10* | (2023.01) | |
| *H04N 23/60* | (2023.01) | |

(52) U.S. Cl.
CPC ............ *A61B 1/063* (2013.01); *A61B 1/0684* (2013.01); *G06T 7/0012* (2013.01); *G06T 7/73* (2017.01); *H04N 23/125* (2023.01); *H04N 23/665* (2023.01); *G06T 2200/24* (2013.01); *G06T 2207/10024* (2013.01); *G06T 2207/10068* (2013.01); *G06T 2207/10152* (2013.01); *G06T 2207/30004* (2013.01)

(56) References Cited

U.S. PATENT DOCUMENTS

| | | | |
|---|---|---|---|
| 2018/0242893 A1 | 8/2018 | Saito | |
| 2021/0007687 A1* | 1/2021 | Gurevich | ............ A61B 6/4417 |
| 2021/0235980 A1 | 8/2021 | Oosake | |
| 2021/0385367 A1* | 12/2021 | Yabe | ...................... G16H 40/67 |

FOREIGN PATENT DOCUMENTS

| | | | | | |
|---|---|---|---|---|---|
| DE | 112023002301 | T5 | 3/2025 | | |
| JP | 2010172673 | | 8/2010 | | |
| JP | 2013507182 | | 3/2013 | | |
| JP | 2013521900 | | 6/2013 | | |
| JP | 2017086303 | | 5/2017 | | |
| KR | 20190076287 | | 7/2019 | | |
| KR | 102393661 | | 5/2022 | | |
| KR | 102393661 | B1 * | 5/2022 | ............ | A61B 5/746 |
| WO | 2011113162 | | 9/2011 | | |
| WO | 2020075578 | | 4/2020 | | |
| WO | 2023224740 | | 11/2023 | | |
| WO | WO-2023219807 | A1 * | 11/2023 | | |

OTHER PUBLICATIONS

"International Application Serial No. PCT US2023 017526, Written Opinion mailed Jul. 17, 2023", 8 pgs.

Dsouza, Alisha V, "Review of fluorescence guided surgery systems identification of key performance capabilities beyond indocyanine green imaging", Journal of Biomedical Optics, SPIE, 1000 20th St. Bellingham WA 98225-6705 USA, vol. 21, No. 8, 1, (Aug. 1, 2016), 80901 pgs.

Gray, Dan, "A compact fluorescence and white light imaging system for intraoperative visualization of nerves", Advanced Biomedical and Clinical Diagnostic Systems X, SPIE, 1000 20th St. Bellingham WA 98225-6705 USA, vol. 8214, No. 1, (Mar. 8, 2012), 1-7.

"International Application Serial No. PCT/US2023/017526, International Preliminary Report on Patentability mailed Nov. 28, 2024", 10 pgs.

"Indian Application Serial No. 202447084084, First Examination Report mailed Nov. 13, 2025", 6 pgs.

"Japanese Application Serial No. 2024-568358, Notification of Reasons for Refusal mailed Apr. 7, 2026", w English Translation, 15 pgs.

* cited by examiner

Figure 5A:
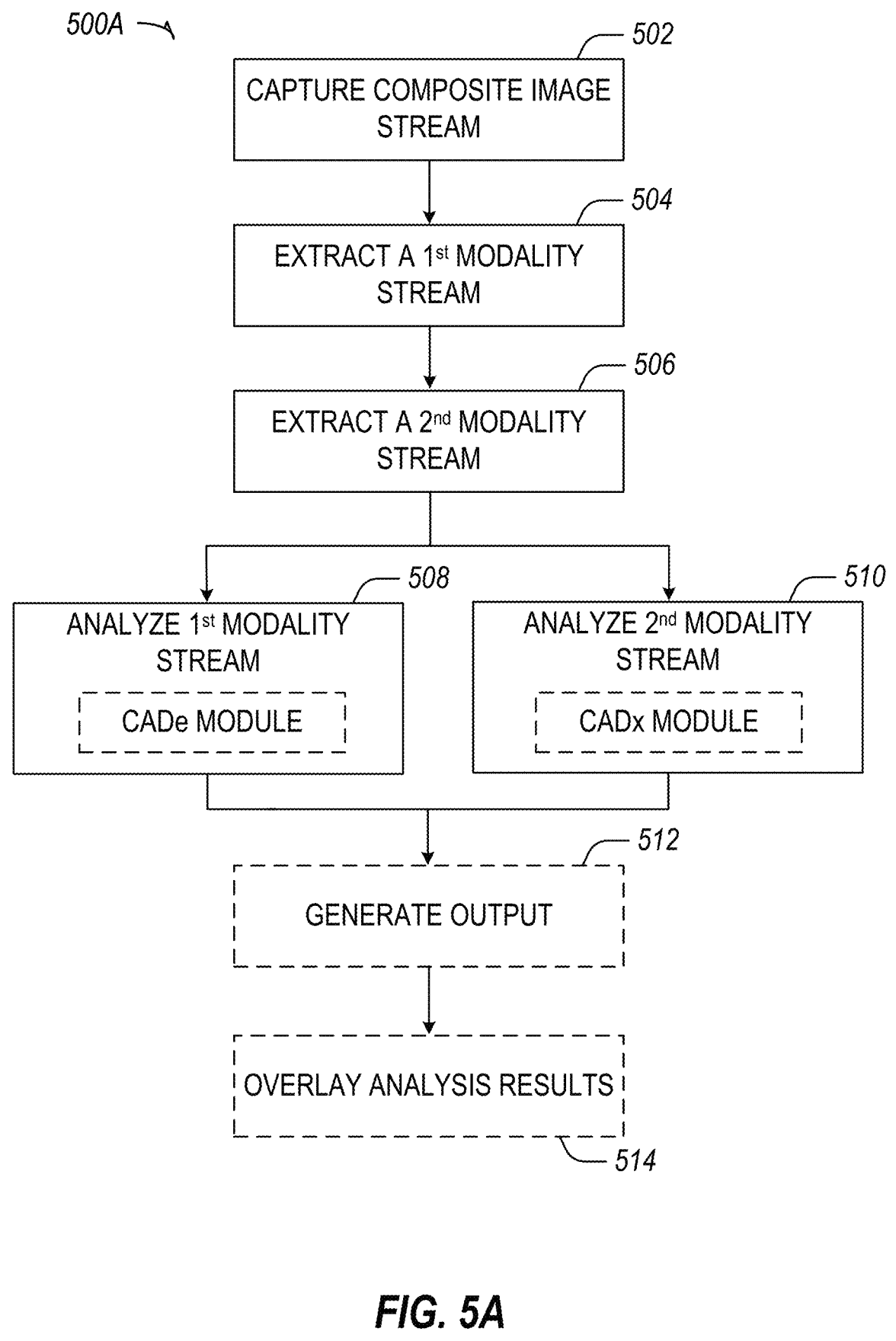

500A

502

CAPTURE COMPOSITE IMAGE
STREAM

504

EXTRACT A 1st MODALITY
STREAM

506

EXTRACT A 2nd MODALITY
STREAM

508

ANALYZE 1st MODALITY
STREAM

CADe MODULE

510

ANALYZE 2nd MODALITY
STREAM

CADx MODULE

512

GENERATE OUTPUT

OVERLAY ANALYSIS RESULTS

CAPTURE COMPOSITE IMAGE STREAM — 502

OPERATE CAMERA AT 60HZ — 520

SYNC 1ST LIGHTING MODALITY @ 30HZ — 522

SYNC 2ND LIGHTING MODALITY @ 30HZ — 524

EXTRACT A 1st MODALITY STREAM — 504

EXTRACT ODD FRAMES FROM COMPOSITE STREAM — 526

EXTRACT A 2nd MODALITY STREAM — 506

EXTRACT EVEN FRAMES FROM COMPOSITE STREAM — 528

TECHNIQUES FOR SIMULTANEOUSLY RUNNING DISCRETE IMAGING MODALITIES

CROSS-REFERENCE TO RELATED APPLICATION

This application claims the benefit of priority to U.S. Provisional Patent Application Ser. No. 63/364,814, filed May 17, 2022, the contents of which are incorporated herein by reference in their entirety.

BACKGROUND

During a typical endoscopic procedure, a health care provider (HCP) may utilize multiple different imaging modalities to gain a full understanding of an anatomy being examined. For example, during a colonoscopy an HCP may manipulate a colonoscope throughout a patient's colon to identify polyps or other structures of interest. While scanning apparently healthy tissues the HCP may rely predominantly on a $1^{st}$ imaging modality such as white light endoscopy (WLE). WLE may involve capturing images of the colon while the full spectrum of visible light is being emitted from the colonoscope. As various instances throughout the colonoscopy, the HCP may elect to manually toggle from the $1^{st}$ imaging modality to a $2^{nd}$ imaging modality. For example, upon identifying an area of interest such as a polyp, the HCP may manually depress a button on the colonoscope to toggle to a Narrow Band Imaging (NBI) modality. NBI may involve capturing images of the colon while a predetermine range of visible light (but not the full spectrum) is being emitted from the colonoscope.

As background, NBI is an optical imaging technology that enhances the visibility of vessels and other tissue on the mucosal surface. NBI works by selectively emitting only specific light wavelengths that are absorbed by hemoglobin and penetrate only the surface of human tissue. As a result, with NBI, capillaries on the mucosal surface are displayed in brown and veins in the submucosa are displayed in cyan on the monitor. NBI is not intended to replace histopathological sampling as a means of diagnosis.

Furthermore, while CADe (Computer Aided Detection) algorithms may identify polyps or other anomalies by analyzing images captured via WLE, many CADx (Computer Aided Diagnosis) algorithms which are designed to classify polyps or other anomalies (e.g., as malignant, benign, etc.) are designed to analyze images captured via NBI.

OVERVIEW

Modern endoscopy devices discretely operate in one imaging modality until manually toggled to another imaging modality. Accordingly, such devices are incapable of simultaneously generating and displaying real-time image feeds to multiple discrete imaging modalities. Furthermore, modern endoscopy devices which discretely operate in one imaging modality until manually toggled to another imaging modality are incapable of simultaneously providing suitable images to CADe and CADx algorithms under circumstances in which these different algorithms require different image types as inputs. Further, systems do exist that can provide multiple simultaneous imaging modalities for display to an operator. However, those systems fail to provide the operator with sufficient mechanisms to leverage the multiple image streams, which results in the operator focusing on only one of the multiple streams.

The present inventors have developed systems and techniques to address these challenges with traditional endoscopic instruments. The systems and techniques discussed herein involve capturing a composite image stream that includes multiple lighting modalities and then concurrently processing frames extracted from the composite image stream using different computer aided detection and diagnosis modules (e.g., multiple machine learning algorithms trained to utilize different lighting modalities).

The inventors have developed multiple different techniques for capturing a composite image stream, extracting lighting modality specific image streams from the composite image stream, and feeding, concurrently, the lighting modality specific image streams to various algorithms (e.g., CADe and CADx modules). The inventors also have development techniques for displaying one of the lighting modality specific image streams, such as a white light image stream, and then overlaying results from both CADe and CADx modules run concurrently on the various lighting modality specific images streams extracted from the composite image stream.

The techniques discussed herein eliminate the need for an HCP to manually toggle between different lighting modalities and provide enhanced flexibility in how results can be presented to an HCP during an endoscopic procedure. The techniques also allow for concurrent analysis of an endoscopic procedure by multiple computer aided analysis algorithms.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5A is a flowchart illustrating a technique for concurrent analysis of multiple image streams taken with different lighting modalities in accordance with at least one example of this disclosure.

DETAILED DESCRIPTION

An endoscopy system which is configured to toggle between multiple imaging modalities automatically and continuously and to generate discrete image streams corresponding to individual ones of the imaging modalities. In this way, the endoscopy system is configured to concurrently generate, and display video streams of an anatomy being imaged in two or more discrete imaging modalities (rather than being limited to operating in only one modality at a time).

In an additional example, an endoscopy system is configured to use time sequential imaging to sequentially read out a color image sensor to generate a plurality of narrow bandwidth images that can be selectively combined to create images representative of a variety of imaging modalities, which can then be used to display video streams of an anatomy being imaged in two or more discrete imaging modalities (see discussion reference to FIGS. 2-3B below).

Figure 1:
FIG. 1 illustrates a block diagram of an example system in accordance with at least one example of this disclosure.
Figure 1:
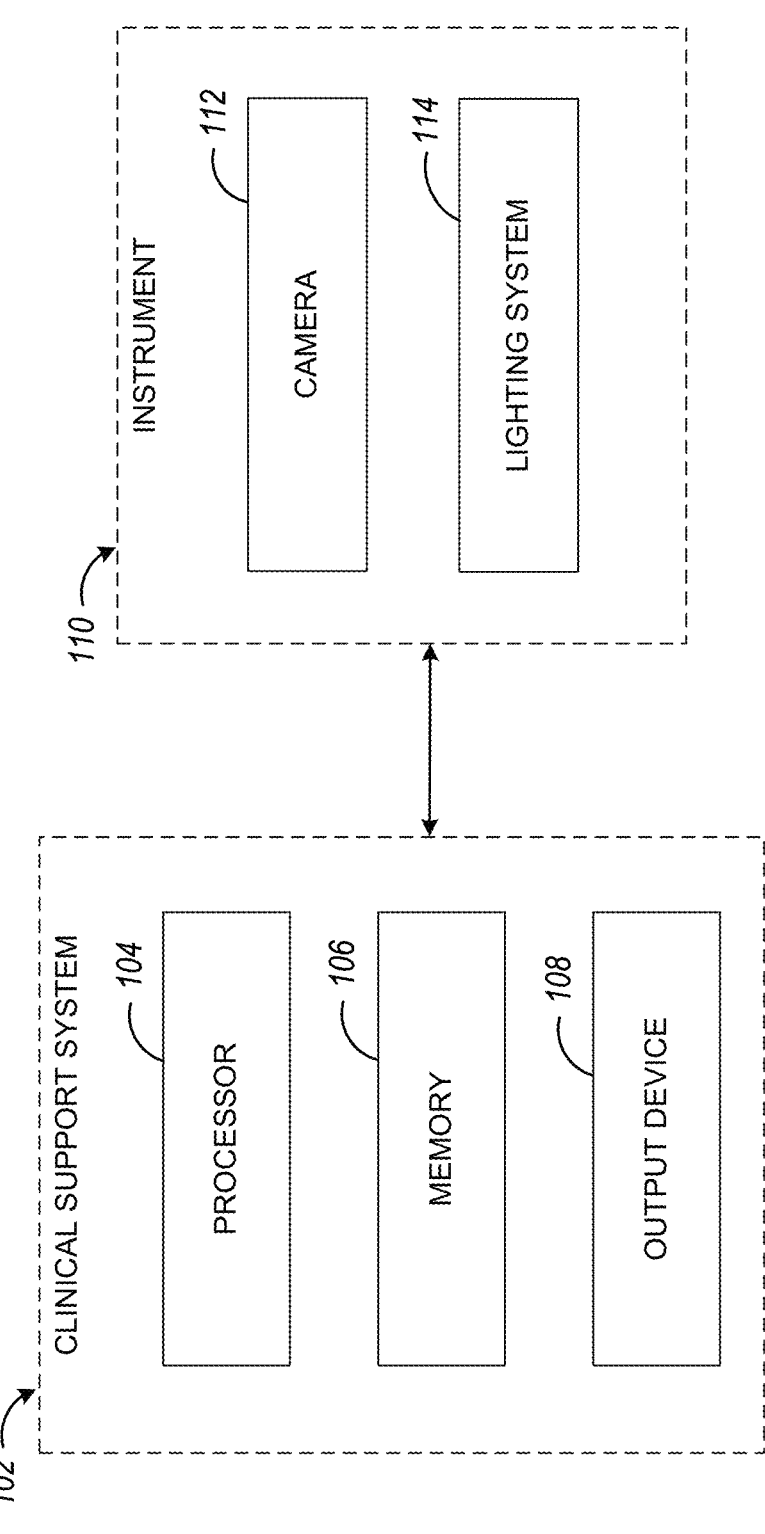

FIG. 1 illustrates a block diagram of an example system 100 in accordance with at least one example of this disclosure. The system 100 represents a minimal system implementation for enabling concurrent multiple lighting modality imaging and concurrent computer aided analysis of the multiple lighting modality image streams. Other examples of a suitable system can include additional processors, dedicated video processors, and/or multiple systems concurrently receiving the composite image stream. In this example, the system 100 can include an instrument 110 and a clinical support system 102. The clinical support system 102 includes a processor 104, a memory device 106, and an output device 108. In this example, the clinical support system 102 can include two-way communication with the instrument 110. The instrument 110 can include a camera 112 and a lighting system 114. In certain examples, the instrument 110 is an endoscopic instrument used in procedures such as a colonoscopy among others.

In this example, the instrument 110 communicates with the clinical support system 102, such as transferring a composite image stream captured by the camera 112 using the lighting system 114. The lighting system 114 operates to enable the camera 112 to capture a composite image that includes two or more image streams where each individual image stream is produced using a selected lighting modality. For example, the composite image stream can include a white light image stream and an NBI image stream. In this example, the clinical support system 102 receives the composite images stream and extracts each of the embedded image streams (e.g., a white light image stream and an NBI image stream). Further details on the operation of the camera 112 and lighting system 114 are discussed below in reference to FIGS. 2-3B.

The clinical support system 102 can include various CADe and CADx modules stored within the memory device 106 for execution by the processor 104 on the extracted image streams. Output from the CADe and CADx modules can be displayed on the output device 108 along with one or more of the extracted images streams. In some examples, the more detailed computing device described in reference to FIG. 6 can be utilized as the clinical support system 102.

Figure 2:
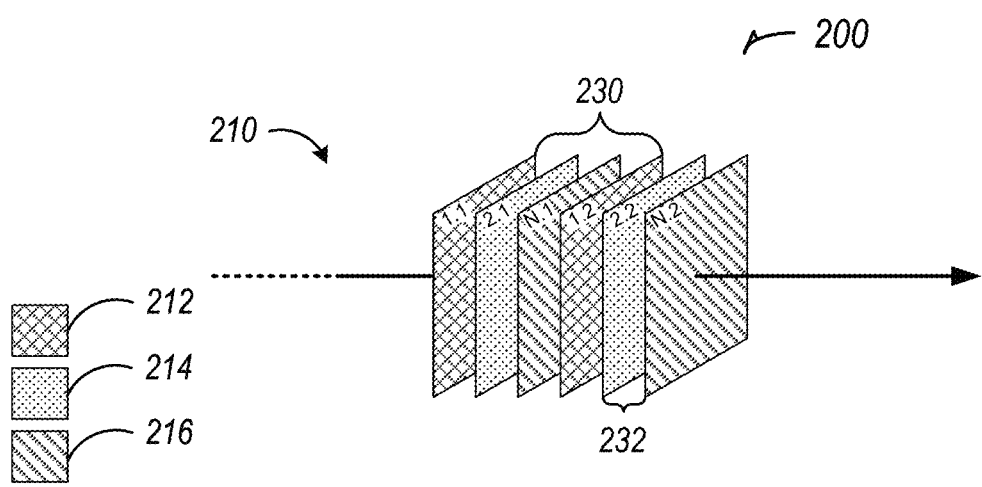
FIG. 2 illustrates an example composite image capture technique in accordance with at least one example of this disclosure.
Figure 2:
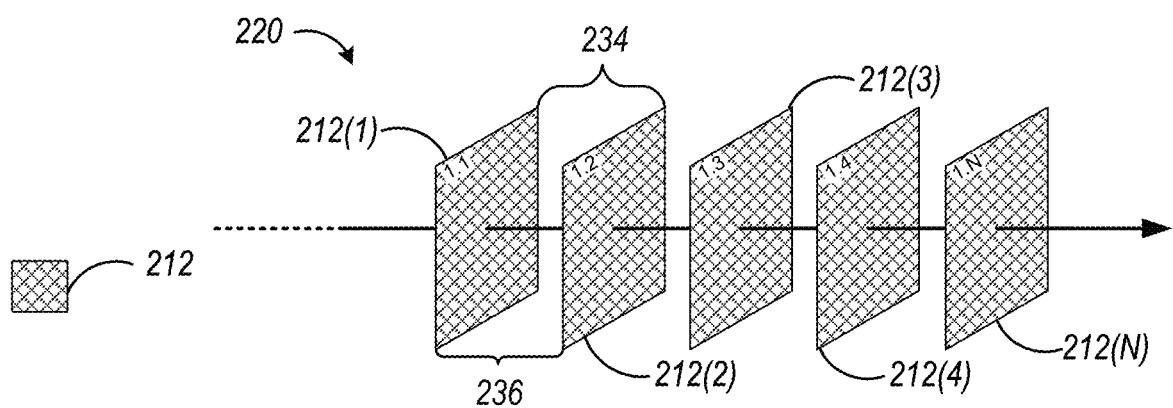
Figure 2:
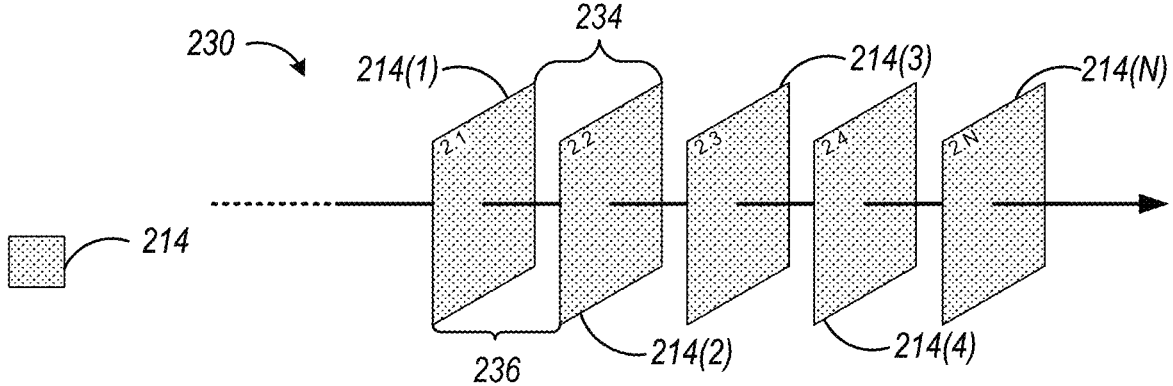

FIG. 2 illustrates an example composite image capture technique 200 in accordance with at least one example of this disclosure. In this example, the composite image stream capture technique 200 synchronizes different lighting modalities with different sequences of frames within the composite image stream. The present disclosure uses the term "interleaved" as a shorthand to describe the multiple image streams created by synchronizing the lighting modality with different sequences of frames within the composite image stream (e.g., a 30 Hz white light image stream interleaved with a 30 Hz NBI image stream in a 60 Hz composite image stream).

In FIG. 2, individual frames within a continuous sequence of frames are labeled as a first modality 212, a second modality 214, and a third modality 216, which are illustrated with distinct cross-hatching and in the format of A.B, where A represents a discrete imaging modality and B represents a sequential frame of that imaging modality within the continuous sequence of frames (1.1., 2.1, 3.1, 1.2, 2.2, . . . etc.).

As illustrated in FIG. 2, the endoscopy system (e.g., system 100) may generate a composite stream 210 which includes image frames that correspond to multiple different imaging modalities. Specifically, the composite stream 210 includes frame 1.1 (a first frame in a sequence of frames captured via a $1^{st}$ imaging modality 212) followed by frame 2.1 (a first frame in a sequence of frames captured via a $2^{nd}$ imaging modality 214), and so on. The endoscopy system can operate at a Full Cycle Frequency 230 which represents the amount of time within which a single image of each imaging modality is captured. Since multiple images are captured within each Full Cycle Frequency 230, the endoscopy system may also be characterized in terms of a Single Frame Frequency 232 which represents the amount of time between individual frames of any lighting modality type. For purposes of the present example, presume that the Full Cycle Frequency 230 is 60 Hz, the endoscopy system is continuously toggling between 3 imaging modalities, and that there is equal timing between each frame within the composite stream 210. Accordingly, based on these parameters, the Single Frame Frequency 232 is 180 Hz. Further presume that the system toggles from the $1^{st}$ imaging modality 212 to the $2^{nd}$ imaging modality 214 to the $3^{rd}$ imaging modality 216 to the $1^{st}$ imaging modality 212, and so on. Other sequences could be implemented. In some examples, the composite stream 210 can include any number of embedded individual modality streams. As lighting modalities such as white light and NBI are in common use within typical endoscopic procedures, other examples discussed herein are limited to discussing two interleaved image streams within the composite image stream.

The endoscopy system may further include a video processor (e.g., processor 104) which is communicatively coupled to the colonoscope (or other type of image capture device), such as instrument 110. Upon receiving the composite stream 210 which includes sequences of frames from all three imaging modalities comingled (e.g., interleaved within the composite stream 210), the video processor parses the frames according to imaging modality to generate discrete streams that uniquely correspond to each imaging modality. In this example, a $1^{st}$ modality stream 220 includes frames captured via the $1^{st}$ imaging modality 212 in the sequential order in which they were captured (e.g., 212(1), 212(2), 212(3), 212(4), . . . 212(N)), whereas a $2^{nd}$ modality stream 230 includes frames captured via the $2^{nd}$ imaging modality 214 in the sequential order in which they were captured (e.g., 214(1), 214(2), 214(3), 214(4), . . . 214(N)). In this example, since the Full Cycle Hz 230 of the composite stream 210 is 60 Hz, the refresh rate of each imaging modality specific stream (e.g., $1^{st}$ modality stream 220, $2^{nd}$ modality stream 230, and $N^{th}$ modality stream [not shown]) is also 60 Hz—which represents a suitable refresh rate for intraprocedural real-time video display. Within the individual lighting modality streams the full frame rate 234 is the same as the individual frame rate 236 (as there are no longer any interleaved additional image streams) In an example, the lighting system 114 for the instrument 100 can include a color wheel to implement the different imaging modalities. The color wheel can be timed to the image sensor frequency of camera 112 to align imaging modality with capture sequence timing.

In another example, the lighting system 114 can include an array of light-emitting diodes (LEDs) or LASER diodes that can be synchronized with a frequency of the camera 112 to produce different lighting modalities. An LED or LASER diode lighting system can be configured to produce narrow-banded light output through selective color activation within the array. Selective activation can be synchronized with sub-frequencies of the camera frequency to result in a combined image stream with multiple image modalities (similar to other examples).

Upon generating the discrete imaging streams 220, 230, through $N^{th}$ modality stream, the video processor may concurrently provide the streams to a display (e.g., output device 108) to enable the HCP to view video streams of multiple different imaging modalities concurrently and without having to manually toggle between imaging modalities. Furthermore, in some embodiments, the video processor may also provide individual ones of the discrete image streams to different image analysis tools which are configured to analyze different types of images. For example, in an embodiment in which the composite stream 210 includes comingled (interleaved) images captured via both WLE and NBI, a discrete image stream corresponding to WLE (e.g., $1^{st}$ modality stream 220) may be provided to a CADe tool (e.g., an AI/ML processing module focused on detection) while a different discrete image stream corresponding to NBI (e.g., $2^{nd}$ modality stream 230) may be provided to a CADx tool (e.g., an AI/ML processing module focused on classification). In this example, artificial intelligence/machine learning models trained from different image modalities can be applied to an image stream simultaneously (concurrently). With results merged into annotated displays provided to the HCP, such as the $1^{st}$ modality stream 220 overlaid with results from both the CADe and CADx tools on output device 108.

In this way, an endoscopy display may present image streams in multiple imaging modalities concurrently while each of these image streams are intelligently annotated in real time with insights provided by specialized CAD tools having different requirements for input image modality. In some embodiments, the endoscopy display (e.g., output device 108) may present a video to the HCP in a $1^{st}$ modality 220 (e.g., full spectrum white light imaging) and may composite or overlay information (e.g., bounding boxes, classifications, etc.) that is obtained by an AI model that analyzes images of a $2^{nd}$ modality 230 (e.g., Narrow Band Imaging). In this way, the HCP may be provided with information that is generated by analyzing an image stream of a non-preferred imaging modality, and this information may be directly composited over of otherwise displayed in association with a different image stream of their preference (e.g., viewing preference). For example, an HCP that prefers to view an endoscopic image stream in full spectrum white light may still obtain valuable insights obtained by enabling the system to concurrently analyze an image stream corresponding to one or more predefined narrower bands of light.

In the example shown in FIG. 2, the different image modalities are generated by timing the light generation associated with each modality to the associated frame capture timing for that modality. Accordingly, in the example described above, a Full Spectrum light generation would occur at 60 Hz, while the NBI imaging light generation also occurring at 60 Hz, but interleaved with the Full Spectrum light, and so on.

Figure 3A:
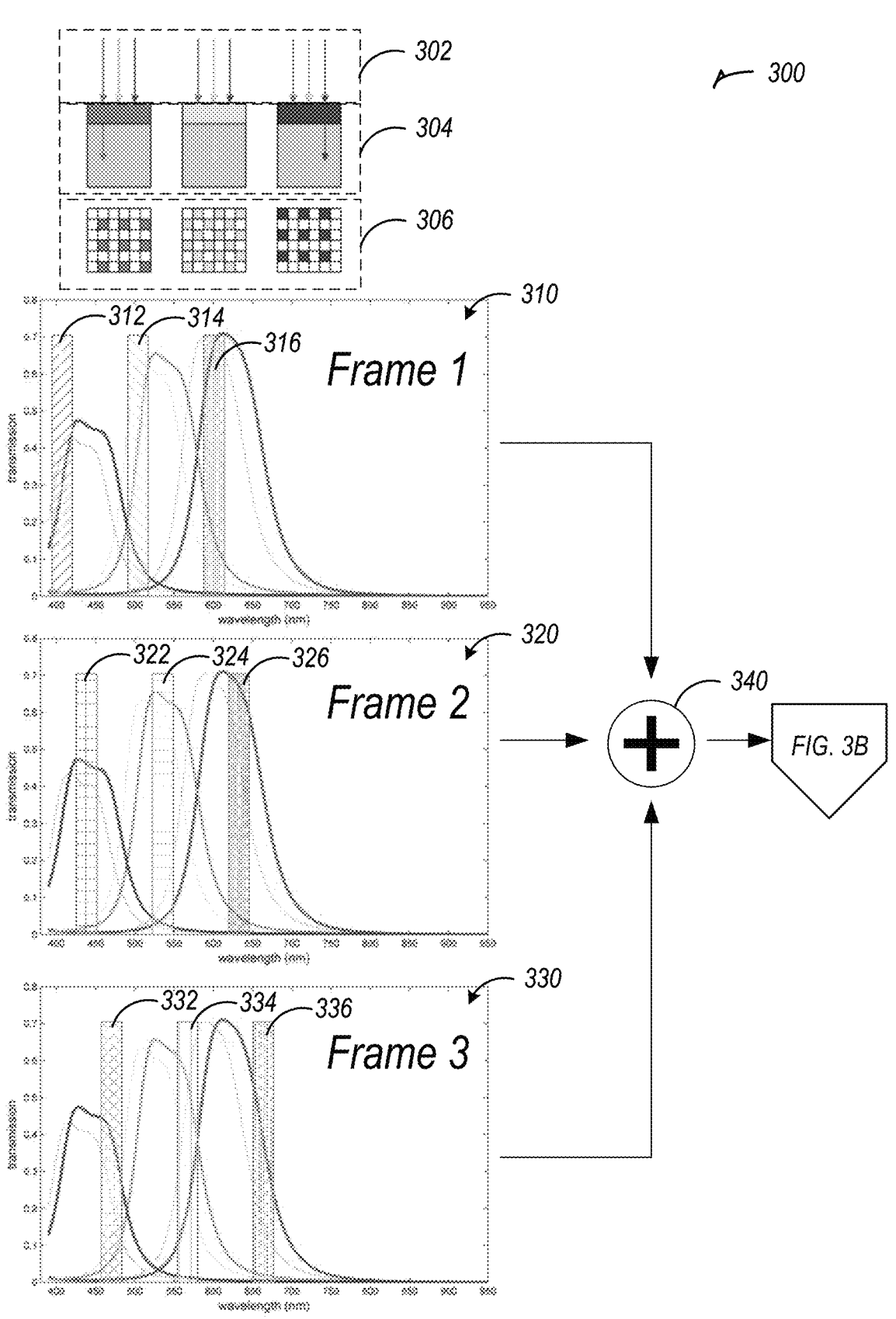
FIGS. 3A-3B illustrate an example composite image capture technique using a color image sensor in accordance with at least one example of this disclosure.
Figure 3B:
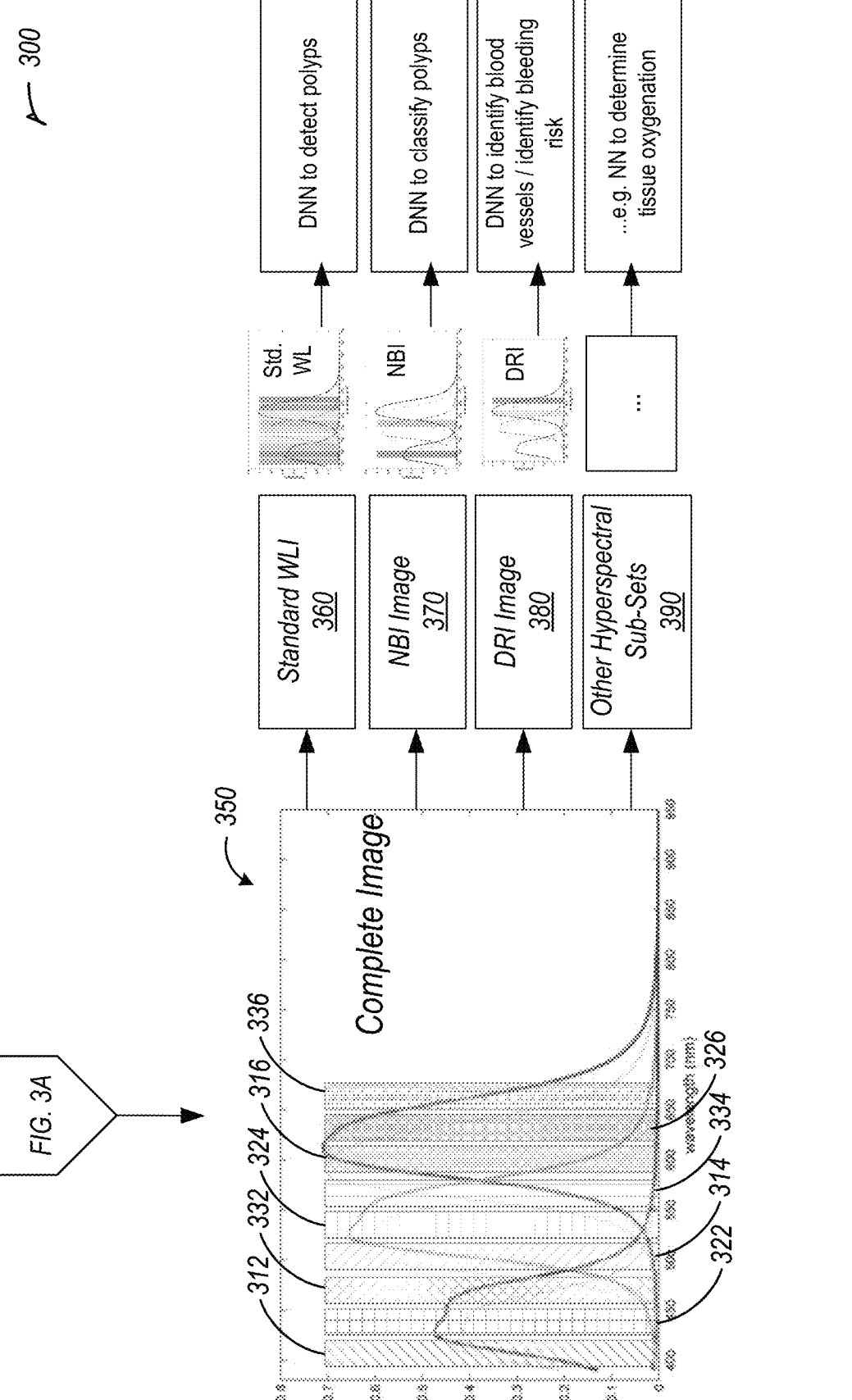

In an additional example, a different, but related, technique can be used to generate a multitude of image modalities as illustrated in FIGS. 3A-3B. FIGS. 3A-3B illustrate an example composite image capture technique using a color image sensor in accordance with at least one example of this disclosure. The approach in this example uses the concept of time sequential images, where images are recorded by an image sensor (e.g., a CCD or CMOS sensor). In Time Sequential Imaging typically a B/W sensor is used to take three consecutive image frames which are illuminated with red, blue, and green light and then an overlay of said three images is used to generate a RGB Image.

In this additional embodiment it is foreseen to use a color sensor instead of a B/W sensor to read-out more narrow spectral bands in each frame by using a color sensor:

a. In case of a primary color sensor, the sensor has three Primary Bands [Red], [Green], [Blue]—and we can distribute several narrow bands within each main color b. In case of a complementary color sensor, the sensor has for Primary Bands [Yellow], [Cyan], [Magenta], [Green]—and we can distribute several narrow bands within each main color The additional embodiment includes splitting-up the sensitive area of each one of the Primary Band into several narrow bands and record those in time-sequential manner. In an example, full spectrum light 302 is run through various filters 304 to produce output patterns on each portion of the RGB sensor 306.

In the outlined example within FIG. 3A, a RGB sensor is used with a total of 9 Bands. (3 Frames*3 Bands per Exposure=9 Bands). In this example, the bands are labeled 312 through 336. It is now foreseen that each of those 9 resulting spatial-spectral datasets is stored in an electrical memory and then can be selectively combined to different imaging modalities. For example, the combination of all 9 data sets can be used to generate a "regular" RGB-Image (e.g., a full spectrum white light image stream). Alternatively selected narrow bands in the green and blue area can be used to generate a NBI Image. Alternatively selected narrow bands in the red area can be used to generate an RDI Image (see FIG. 3B for an illustration).

In this example, Frame 1 (310) includes red band 312, green band 314, and blue band 316, Frame 2 (320) includes red band 322, green band 324, and blue band 326, and Frame 3 (330) includes red band 332, green band 334, and blue band 336. In this example, each of the red bands (312, 322, 332) include a narrow range of color frequency within the sensitivity of the red portion of the RGB sensor. Similarly, each of the green bands (314, 324, 334) and blue bands (316, 326, 336) are each narrow frequency bands within the green and blue portions of the RGB sensor respectively. All the narrow bands within frames 310, 320, and 330 are combined at operation 340 to form a composite image stream 350 (illustrated in FIG. 3B).

Once the composite image stream 350 is generated, the processor 104 within the clinical support system 100 can be used to generate a wide variety of different modality specific image streams. In this example, the processor 104 can extract a standard WLI (white light image) stream 360 by selecting all the bands within the composite image stream 350. Concurrently, the processor 104 can select fewer bands to produced other specialized image modalities, such as NBI stream 370 or dual-red imaging (DRI) stream 380. Other hyperspectral sub-sets can be selected to produce a wide variety of image streams (represented by image stream 390). As illustrated in FIG. 3B, each of the different image streams can be concurrently produced and concurrently used for various specific computer-aided processing to detect and diagnosis anomalies.

It is foreseen that several imaging modalities can be provided in parallel, e.g., to different displays, to different areas of a display, to be overlaid with wrong-color representation or to be handed over to different algorithms for further analysis, e.g., for CADe or CADx applications. For example, as illustrated in FIG. 3B, the different image modalities can be processed by different dedicated neural networks (DNN) to produce different outputs, such as detecting polyps, classifying polyps, identifying blood vessels and/or identifying bleeding risks as well as a Neural Network to determine tissue oxygenation, among other types of processing.

Figure 4:
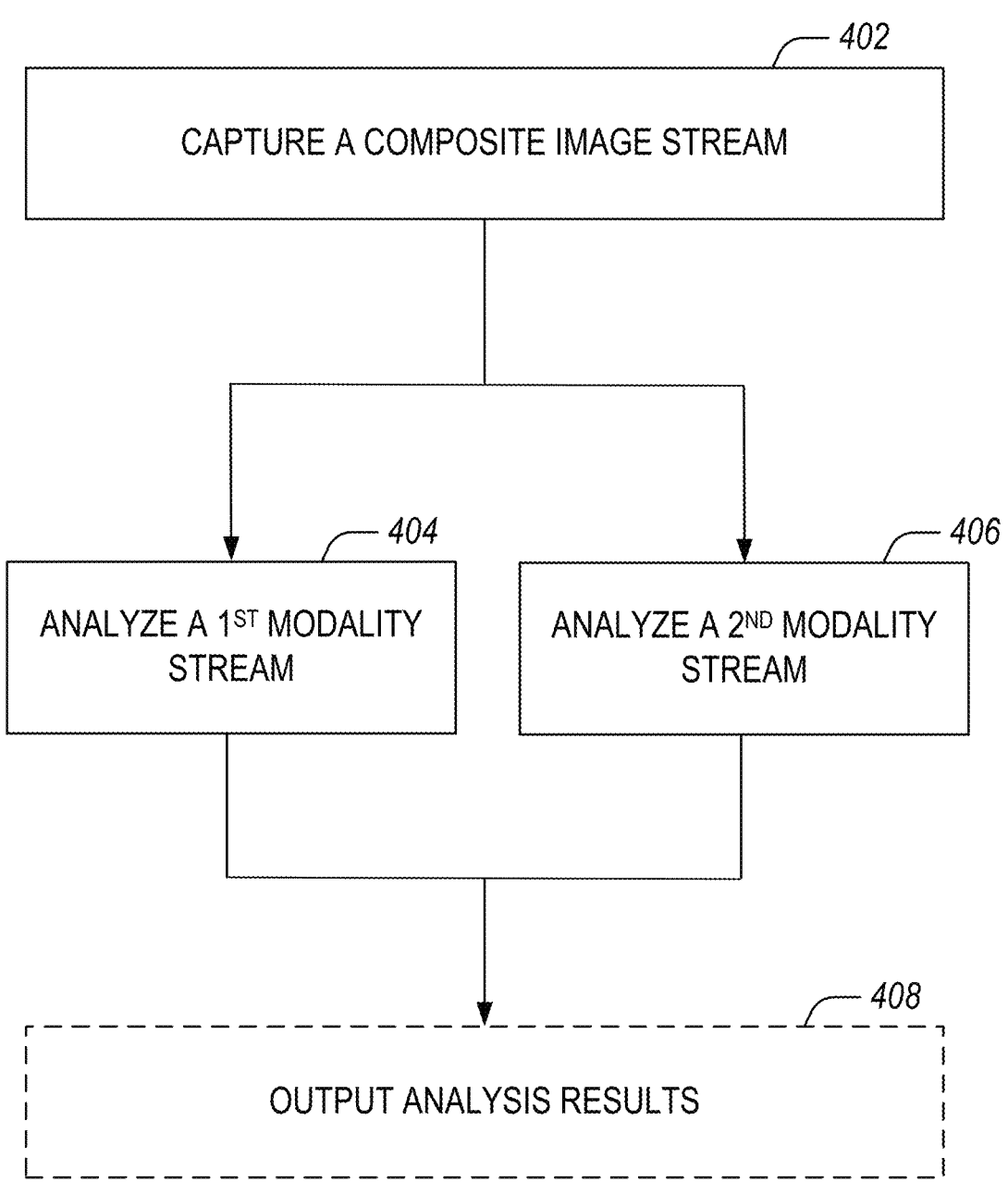
FIG. 4 is a flowchart illustrating a technique for concurrent analysis of multiple image streams taken with different lighting modalities in accordance with at least one example of this disclosure.

FIG. 4 is a flowchart illustrating a technique 400 for concurrent analysis of multiple image streams taken with different lighting modalities in accordance with at least one example of this disclosure. In this example, the technique 400 can include operations such as capturing a composite image stream at 402, analyzing a first modality stream at 404 and concurrently analyzing a second modality stream at 406 as well as optionally outputting analysis results at 408. The technique 400 is discussed in reference to system 100 illustrated in FIG. 1.

In an example, the technique 400 can begin at 402 with the camera 112 and lighting system 114 operating together to capture a composite image stream. At 404, the technique 400 continues with the clinical support system 102 using processor 104 to analyze a first modality stream extracted from the composite image stream captured at 402. At 406, the technique 400 operates concurrently with operation 404 with the clinical support system 102 using the processor 104 to analyze a second modality stream extracted from the composite image stream. At 408, the technique 400 can optionally conclude with the clinical support system 102 outputting analysis results from operations 404 and 406 via output device 108.

In some examples, operation 408 can include outputting for an HCP the first modality stream and/or the second modality stream on the output device 108. Additionally, analysis results from operations 404 and 406 can include identification and/or classification of anomalies overlaid on the $1^{st}$ or $2^{nd}$ modality image stream or on adjacent portions of a display screen. For example, a CADe analysis on the $1^{st}$ modality stream at 404 can generate a bounding box around the identified anomaly while also concurrently displaying a classification of the anomaly generated by a CADx analysis of the second modality stream at 406.

FIG. 5A is a flowchart illustrating a technique 500 for concurrent analysis of multiple image streams taken with different lighting modalities in accordance with at least one example of this disclosure. In this example, the technique 500 can include operations such as capturing a composite image stream at 502, extracting a $1^{st}$ modality stream at 504, extracting a $2^{nd}$ modality stream at 506, and concurrently analyzing the $1^{st}$ and $2^{nd}$ modality streams at 508 and 510 respectively. The technique 500 can also optionally include operations to generate an output at 512 and overlay analysis results at 514. Note, while not illustrated as parallel or concurrent operations, extracting the $1^{st}$ and $2^{nd}$ modality streams at operations 504 and 506 can be done concurrently within a system such as system 100. The generation of an output at 512 can also comprise an either automatic selection of the modality stream to be displayed on an output device based on the analysis results, or the suggestion to the operator to select a particular modality stream for display.

For example, if a detection algorithm detects a potential finding in the first stream and the characterization algorithms characterizes this finding as a disease, the system can switch to the second modality stream or suggest to the operator to display the second modality stream. Alternatively, it is also envisioned, while not explicitly illustrated, that the system can generate a hybrid or augmented output in which the image is shown in a first modality stream, but specific areas of the image are overlaid with the corresponding area of the second modality stream, or where a cropped and magnified area of the second modality stream is displayed in a picture-in-picture configuration. For example, the system might display a white light image, but will then overlay the area of a detected adenoma with the corresponding NBI image, or it will show the white light image, and show a magnified view of an area of interest, corresponding to the location of a detected polyp in a smaller picture next the white light image.

In this example, the technique 500 can begin at 502 with the camera 112 and lighting system 114 capturing a composite image stream. At 504, the technique 500 can continue with the processor 104 extracting a $1^{st}$ modality stream from the composite image stream received from camera 112. The technique 500 can continue by extracting a $2^{nd}$ modality stream at 506. At operations 508 and 510, the technique 500 can concurrently analyze the $1^{st}$ modality stream and the $2^{nd}$ modality stream. In an example, the $1^{st}$ modality stream is analyzed at 508 using a CADe module operating on the clinical support system 102. The $2^{nd}$ modality stream can be analyzed at 510 using a CADx module concurrently operating on the clinical support system 102.

At 512, the technique 500 can optionally continue with the clinical support system 102 generating output which can include one or more of the $1^{st}$ and $2^{nd}$ modality streams and analysis results from operations 508 and 510. At 514, the technique 500 can optionally conclude with the clinical support system 102 overlaying analysis results from the CADe and/or CADx operations at 508 and 510 on an output display.

Figure 5B:
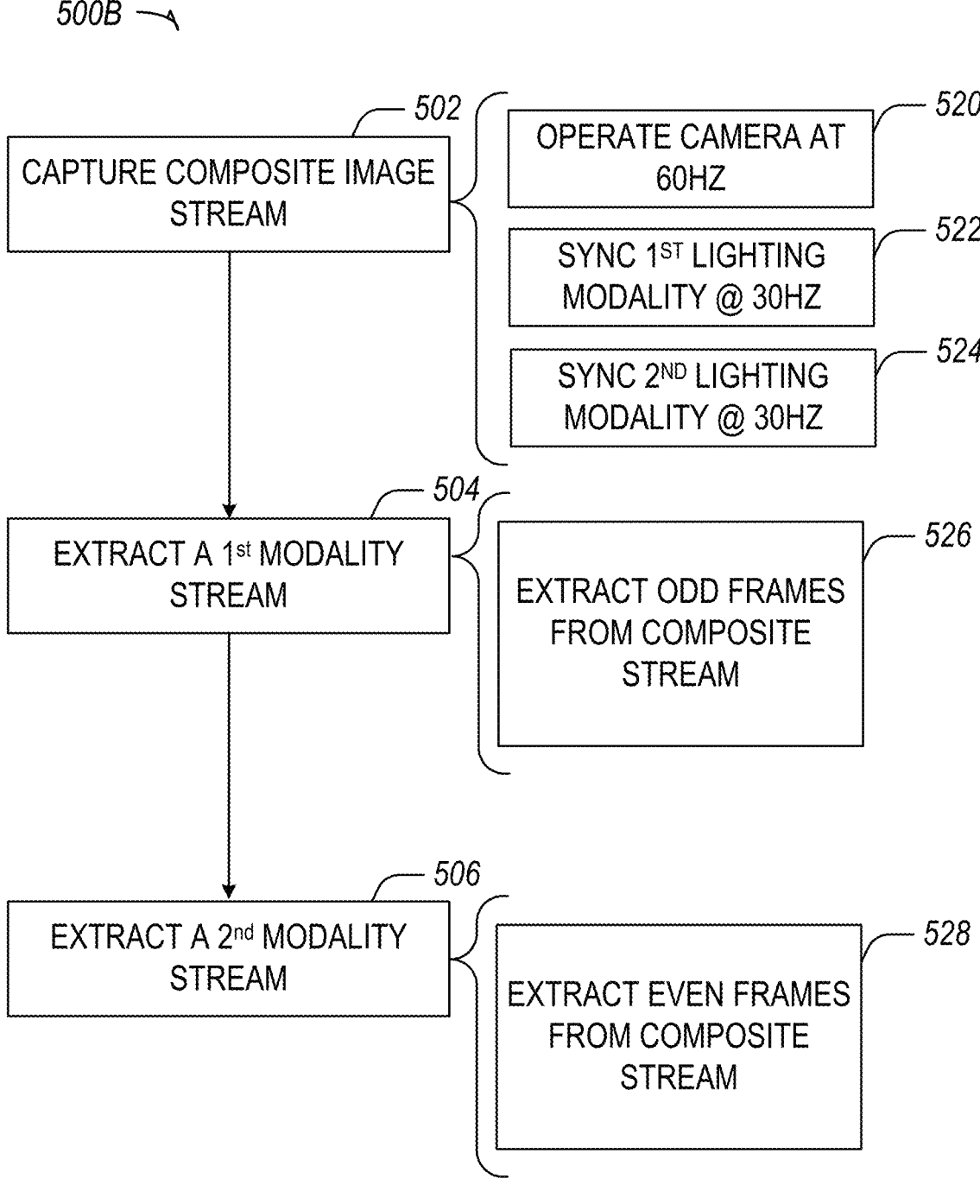
FIGS. 5B-5C are partial flowcharts illustrating variations on a technique for different composite image stream generation and extraction in accordance with at least one example of this disclosure.
Figure 5C:
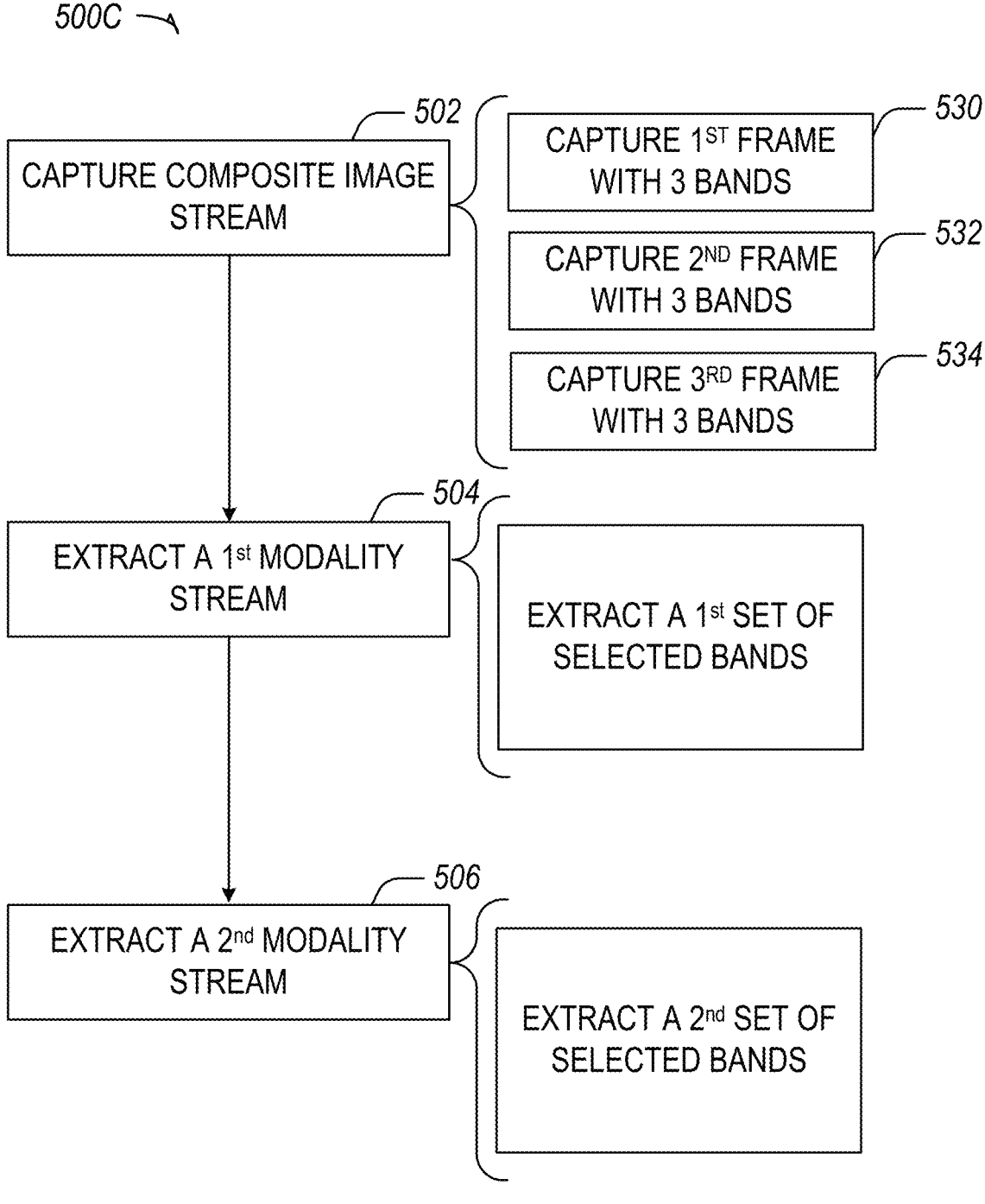

FIGS. 5B-5C are partial flowcharts illustrating variations on technique 500 for different composite image stream generation and extraction in accordance with at least one example of this disclosure. FIG. 5B illustrates a variation on technique 500 that aligns with the imaging technique discussed in reference to FIG. 2. The technique 500B can include specific implementations of operations 502, 504, and 506 from technique 500. In this example, the technique 500B can begin at 502 with operations including operating camera 112 at 60 Hz at 520, synchronizing a $1^{st}$ lighting modality at 522 and synchronizing a $2^{nd}$ lighting modality at 524. In this example, the camera 112 is operated at a full frame rate of 60 Hz and will include two interleaved modality streams each at 30 Hz. At 504, the technique 500B can continue by extracting the $1^{st}$ modality stream from the composite stream by selecting odd frames from the composite stream at 526 (where the odd frames were each captured using a $1^{st}$ lighting modality in operation 520). At 506, the technique 500B continues with the processor 104 extracting the $2^{nd}$ modality stream from the composite image stream by extracting even frames from the composite stream at 528.

FIG. 5C illustrates a second variation on technique 500 that aligns with the imaging technique discussed in reference to FIGS. 3A and 3B. The technique 500C can include specific implementations of operations 502, 504, and 506 similar to technique 500B discussed above. In this example, the technique 500C can being at 502 with operations to capture a composite image including capturing a $1^{st}$ frame with 3 narrow frequency bands at 530, capturing a $2^{nd}$ frame with a second set of 3 narrow frequency bands at 532, and capturing a $3^{rd}$ frame with a third set of 3 narrow frequency bands at 534. As discussed in reference to FIGS. 3A and 3B, the sets of frequency bands in this example related to the red, green, and blue portions of an RGB camera sensor. Capturing of the three different frames in operations 530, 532, and 534 are repeated at the frame rate of the camera to generate the composite image stream at 502. At 504, the technique 500C can continue with the clinical support system 102 extracting a $1^{st}$ modality stream from the composite stream captured at 502. In this example, the operation 504 can include extracting a first set of selected bands from the composite image stream to form a $1^{st}$ modality stream. In an example, the first set of selected bands can include all nine bands captured in operations 530, 532, and 534 to form a WLI modality. At 506, the technique 500C can continue with the clinical support system 102 extracting a $2^{nd}$ modality stream from the composite stream. In this example, the operation 506 van include extracting a second set of selected bands from the composite image, such as narrow bands within red and green frequency ranges to form an NBI modality stream. As discussed above in reference to FIG. 3B, the technique 500C can be modified to extract more than two different modality streams by concurrently selecting additional sets of selected bands. The various modality streams can be generated concurrently and be fed to various analysis modules that can also be run concurrently as discussed above.

Figure 6:
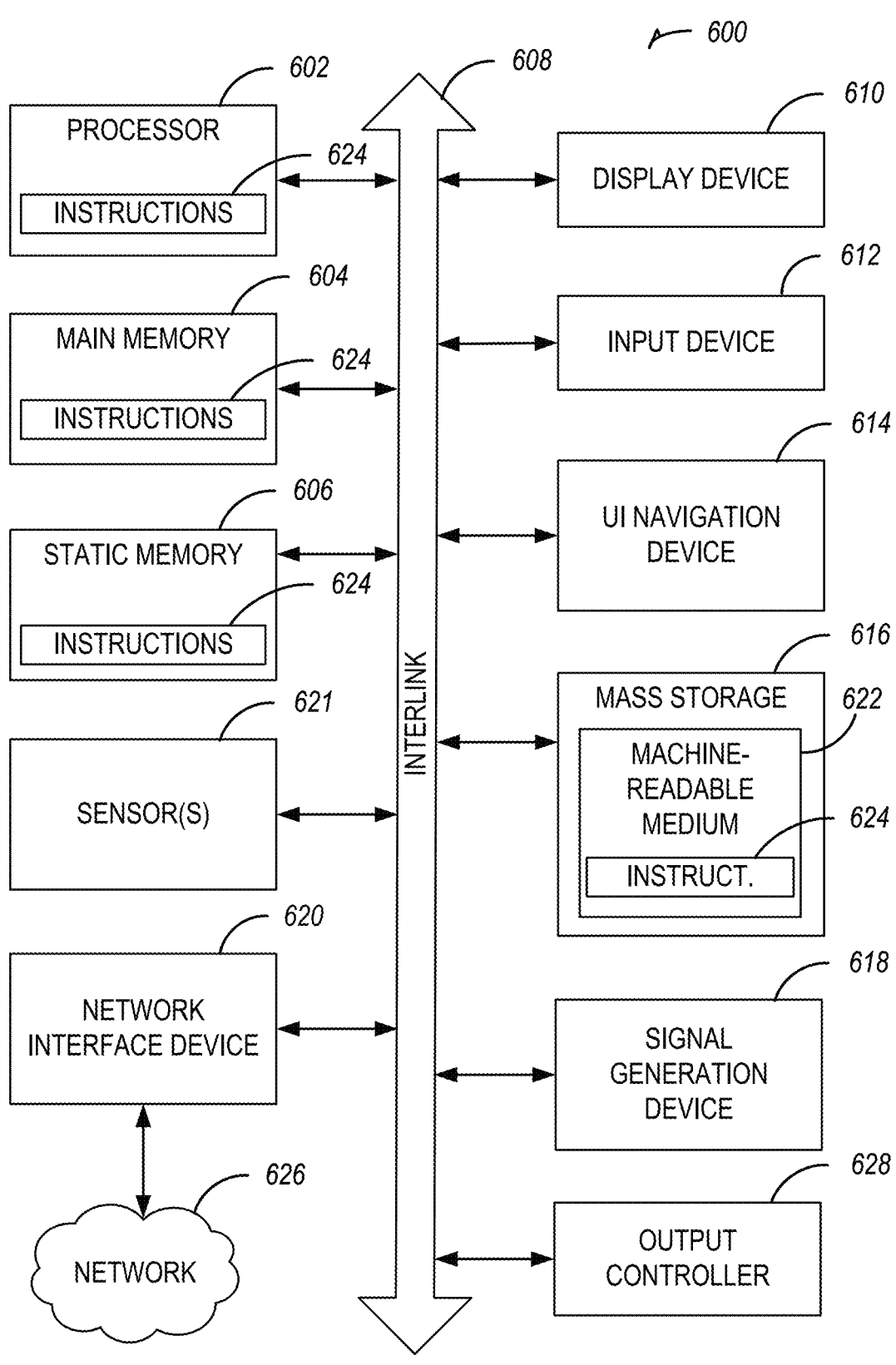
FIG. 6 illustrates a block diagram of an example machine upon which any one or more of the techniques discussed herein may perform in accordance with at least one example of this disclosure.

FIG. 6 illustrates a block diagram of an example machine 600 upon which any one or more of the techniques (processes) discussed herein may perform in accordance with some embodiments. The example machine 600 can also be used within the system 100 discussed above in reference to FIG. 1 as a clinical support system. In alternative embodiments, the machine 600 may operate as a standalone device and/or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610, an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., Universal Serial Bus (USB), parallel, or other wired or wireless (e.g., infrared (IR), near field communication (NFC), etc.) connection to communicate and/or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624. The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 600, and includes digital or analog communications signals or other intangible medium to facilitate communication of such software.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method for simultaneously analyzing multiple imaging modalities, the method comprising:

capturing a combined image stream including a first modality stream and at least a second modality stream;

analyzing the first modality stream with a first analysis module;

analyzing, concurrently with the analyzing the first modality stream, the second modality stream with a second analysis module; and generating a graphical output display including images from the first modality stream with output from the second analysis module overlaid on the images from the first modality stream including selectively displaying specific areas of the second modality stream in a picture-in-picture configuration based on output from the second analysis module, wherein the first modality stream is a white light, wherein output from the first analysis module includes identification of an abnormality and output from the second analysis module includes classification of the abnormality, wherein the selectively displaying specific areas of the second modality stream in the picture-in-picture configuration includes displaying a magnified view of the abnormality from the second modality stream.

2. The method of claim 1, wherein the first analysis module is a computer aided identification module, and wherein the second analysis module is a computer aided classification module.

3. The method of claim 2, wherein the analyzing the first modality stream with the computer aided identification module includes applying a first machine learning model against the first modality stream.

4. The method of claim 2, wherein the analyzing the second modality stream with the computer aided classification module includes applying a second machine learning model against the second modality stream.

5. The method of claim 2, wherein the generating the graphical output display includes using output from the first analysis module to position the output from the second analysis module overlaid on the images from the first modality stream.

6. The method of claim 5, further comprising concurrently overlaying results from the computer aided identification module and the computer aided classification module on a display screen.

7. The method of claim 2, further comprising outputting, concurrently:

an identification output generated by the computer aided identification module; and

a classification output generated by the computer aided classification module.

8. The method of claim 7, wherein the outputting, concurrently, includes overlaying at least one of the identification output and the classification output the first modality stream.

9. The method of claim 1, wherein the outputting the identification includes outputting a region of interest identifying a location of the abnormality.

10. The method of claim 1, wherein the capturing the combined image stream includes capturing at least a 50 Hz image stream including a first 25 Hz image stream and a second 25 Hz image stream interleaved with the first 25 Hz image stream.

11. The method of claim 10, wherein the capturing the combined image stream includes parsing out the first 25 Hz image stream as the first modality stream and the second 25 Hz image stream as the second modality stream.

12. The method of claim 1, wherein the capturing the combined image stream includes capturing a first portion of the combined image stream with a first lighting modality and capturing a second portion of the combined image stream with a second lighting modality, wherein the first portion and the second portion are interleaved.

13. The method of claim 1 wherein the capturing the combined image stream includes synchronizing a color wheel with a sensor frequency of a sensor used to capture the combined image stream, wherein the color wheel includes a first set of filters to generate a first imaging modality corresponding to the first modality stream and a second set of filters to generate a second imaging modality corresponding to the second modality stream.

14. The method of claim 1, wherein the capturing the combined image stream includes synchronizing light-emitting diodes or LASER diodes with a sensor frequency of a sensor used to capture the combined image stream, wherein the light-emitting diodes or LASER diodes are configured to generate a first imaging modality corresponding to the first modality stream and a second imaging modality corresponding to the second modality stream.

15. The method of claim 1, further comprising outputting, concurrently, the first modality stream and the second modality stream to a user interface device.

16. The method of claim 1, wherein the capturing the combined image stream includes:

capturing a full frame rate image using a primary color sensor;

distributing a plurality of narrow color bands within three primary bands generated by the primary color sensor;

selecting a first subset of bands from the plurality of narrow color bands to generate the first modality stream; and selecting a second subset of the bands from the plurality of narrow color bands to generate the second modality stream.

17. The method of claim 16, wherein the capturing the combined image stream includes selecting a third subset of bands from the plurality of narrow color bands to generate a third modality stream.

18. The method of claim 1, wherein the capturing the combined image stream includes:

capturing a full frame rate image using a complementary color sensor;

distributing a plurality of narrow color bands within four primary bands generated by the complementary color sensor;

selecting a first subset of bands from the plurality of narrow color bands to generate the first modality stream; and selecting a second subset of the bands from the plurality of narrow color bands to generate the second modality stream.

19. A system comprising:

an endoscope with a camera and a lighting system, the camera and the lighting system configured to generate a first modality stream and a second modality stream;

a processor and a memory device, the memory device including instructions that, when executed by the processor, cause the processor to perform operations comprising:

capturing a combined image stream including a first modality stream and at least a second modality stream;

analyzing the first modality stream with a first analysis module;

analyzing, concurrently with the analyzing the first modality stream, the second modality stream with a second analysis module; and outputting, based on analyzing the first modality stream and analyzing the second modality stream, a recommended image stream and overlaying results from the first analysis module and the second analysis module on the recommended image stream including overlaying specific areas of the second modality stream onto corresponding areas of the first modality stream based on output from the second analysis module, wherein output from the first analysis module includes identification of an abnormality and output from the second analysis module includes classification of the abnormality, and wherein overlaying specific areas of the second modality stream includes overlaying an area of the abnormality with a corresponding area of second modality stream.

20. The system of claim 19, wherein the instructions cause the processor to perform operations further comprising:

selecting, based on analyzing the first modality stream and analyzing the second modality stream, a display modality stream from the first modality stream and the second modality stream; and displaying the display modality stream on a display device.

21. The system of claim 19, wherein the instructions cause the processor to perform operations further comprising:

generating, based on analyzing the first modality stream and analyzing the second modality stream, a hybrid image that selectively combines outputs of the first modality stream and the second modality stream.

* * * * *